(12) United States Patent
Ashe et al.

(10) Patent No.: US 7,008,133 B2
(45) Date of Patent: Mar. 7, 2006

(54) DISPOSABLE SINGLE-USE APPLICATOR

(75) Inventors: Gary Ashe, Sanborn, NY (US);
Edward M. Purizhansky, Williamsville, NY (US)

(73) Assignee: TMP Technologies, Inc., Buffalo, NY (US)

( * ) Notice: Subject to any disclaimer, the term of this patent is extended or adjusted under 35 U.S.C. 154(b) by 0 days.

(21) Appl. No.: 10/635,013

(22) Filed: Aug. 5, 2003

(65) Prior Publication Data
US 2004/0156668 A1      Aug. 12, 2004

Related U.S. Application Data

(60) Provisional application No. 60/406,544, filed on Aug. 28, 2002.

(51) Int. Cl.
*B43K 5/14*        (2006.01)
(52) U.S. Cl. ........................................ 401/132; 401/133
(58) Field of Classification Search ................ 401/132, 401/133, 140, 203, 204; 15/244.1, 244.4, 15/247; 604/1–3; 206/209, 223
See application file for complete search history.

(56) References Cited

U.S. PATENT DOCUMENTS

| | | | |
|---|---|---|---|
| 3,027,999 A * | 4/1962 | Heroy, Jr. .................... 206/223 |
| 3,079,628 A * | 3/1963 | Wright ......................... 401/204 |
| 3,082,468 A * | 3/1963 | Wattles ........................ 401/132 |
| 3,366,988 A * | 2/1968 | Ginter et al. ............... 15/244.1 |
| 3,690,448 A * | 9/1972 | Switzer ....................... 206/361 |
| 4,155,139 A * | 5/1979 | Corcoran .................... 15/244.1 |
| 4,469,223 A * | 9/1984 | Smith .......................... 206/209 |
| 4,732,287 A * | 3/1988 | Bennett ........................ 401/132 |
| 4,913,682 A | 4/1990 | Shabo ............................ 604/1 |
| 4,952,204 A | 8/1990 | Korteweg ........................ 604/1 |
| 5,032,188 A * | 7/1991 | Kettle et al. ................. 206/209 |
| 5,138,738 A * | 8/1992 | Nicholson ..................... 15/247 |
| 5,152,742 A | 10/1992 | Simpson ......................... 604/3 |
| 5,704,906 A | 1/1998 | Fox ................................ 604/1 |
| 5,991,960 A | 11/1999 | Johnson ..................... 15/210.1 |
| 6,138,313 A * | 10/2000 | Barton et al. ............... 15/143.1 |
| 6,155,990 A | 12/2000 | Fournier ...................... 600/572 |
| 6,516,947 B1 * | 2/2003 | Van Dyke et al. .............. 604/1 |
| 6,669,389 B1 * | 12/2003 | Gueret ......................... 401/122 |
| 2001/0000205 A1 | 4/2001 | Hague et al. ............... 215/201 |

* cited by examiner

*Primary Examiner*—Tuan Nguyen
(74) *Attorney, Agent, or Firm*—Walter W. Duft

(57) ABSTRACT

A disposable single-use applicator assembly includes a package that sealably contains a fluid to be dispensed in and around an applicator for dispensing the fluid. The applicator has a handle and a fluid holding element at a first end portion of the handle. Prior to use, the fluid holding element is disposed in the package that contains the dispensable fluid. A hermetic closure is provided between a first end portion of the package and an intermediate portion of the handle. A second end portion of the handle extends clear of the package. A breakable portion of the package proximate to the hermetic closure allows the fluid holding element to be withdrawn from the package and thereby uncovered for use.

8 Claims, 4 Drawing Sheets

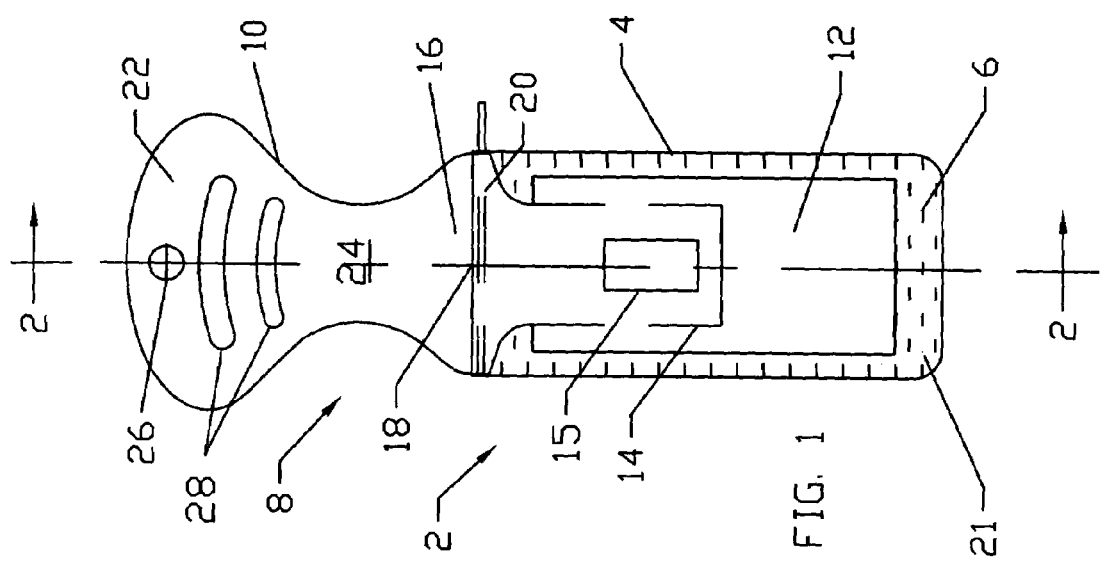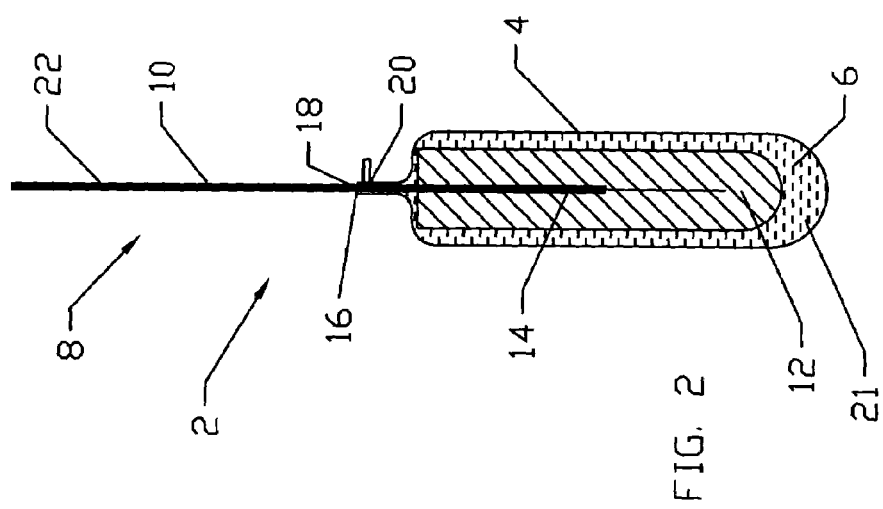

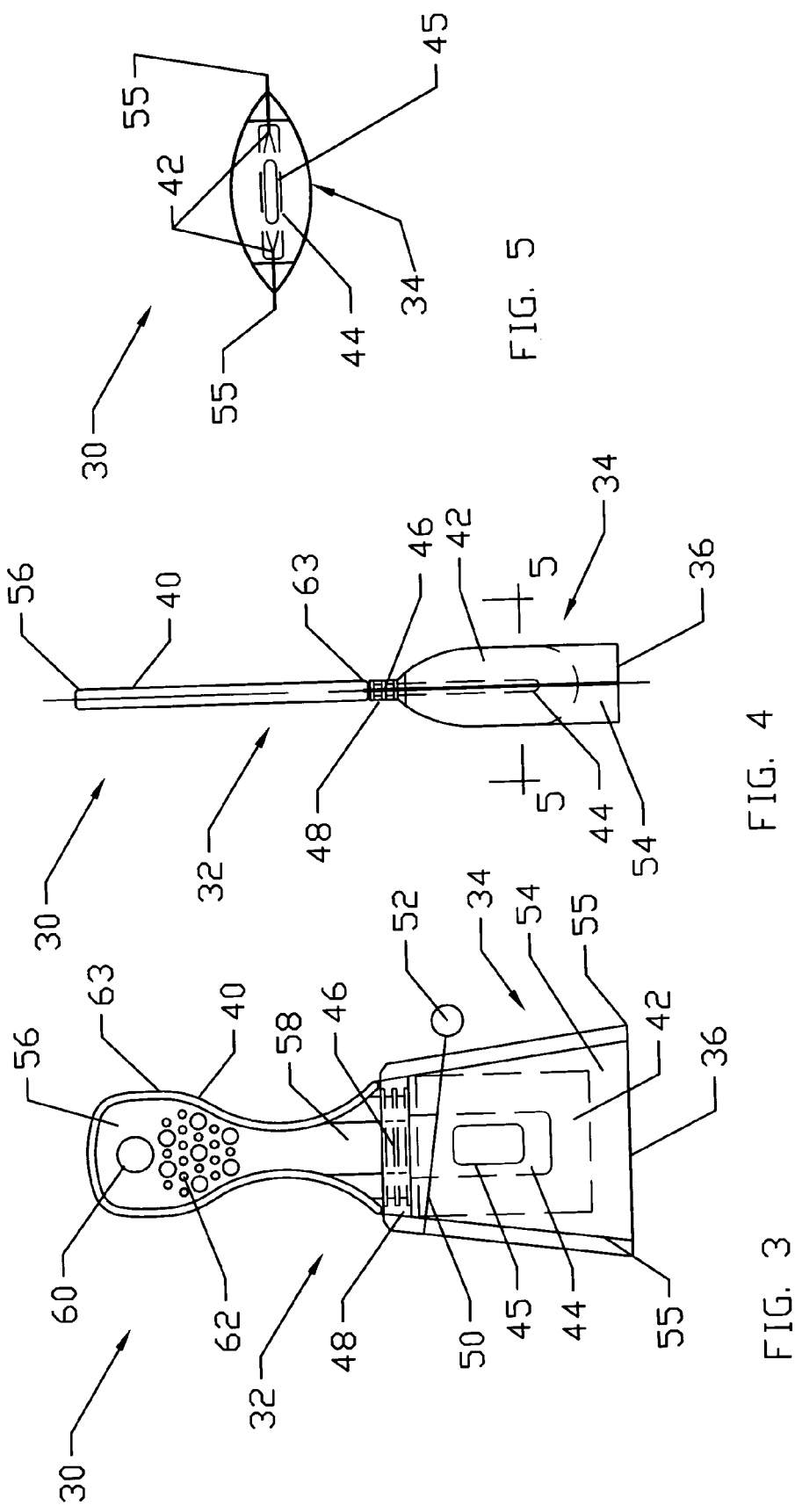

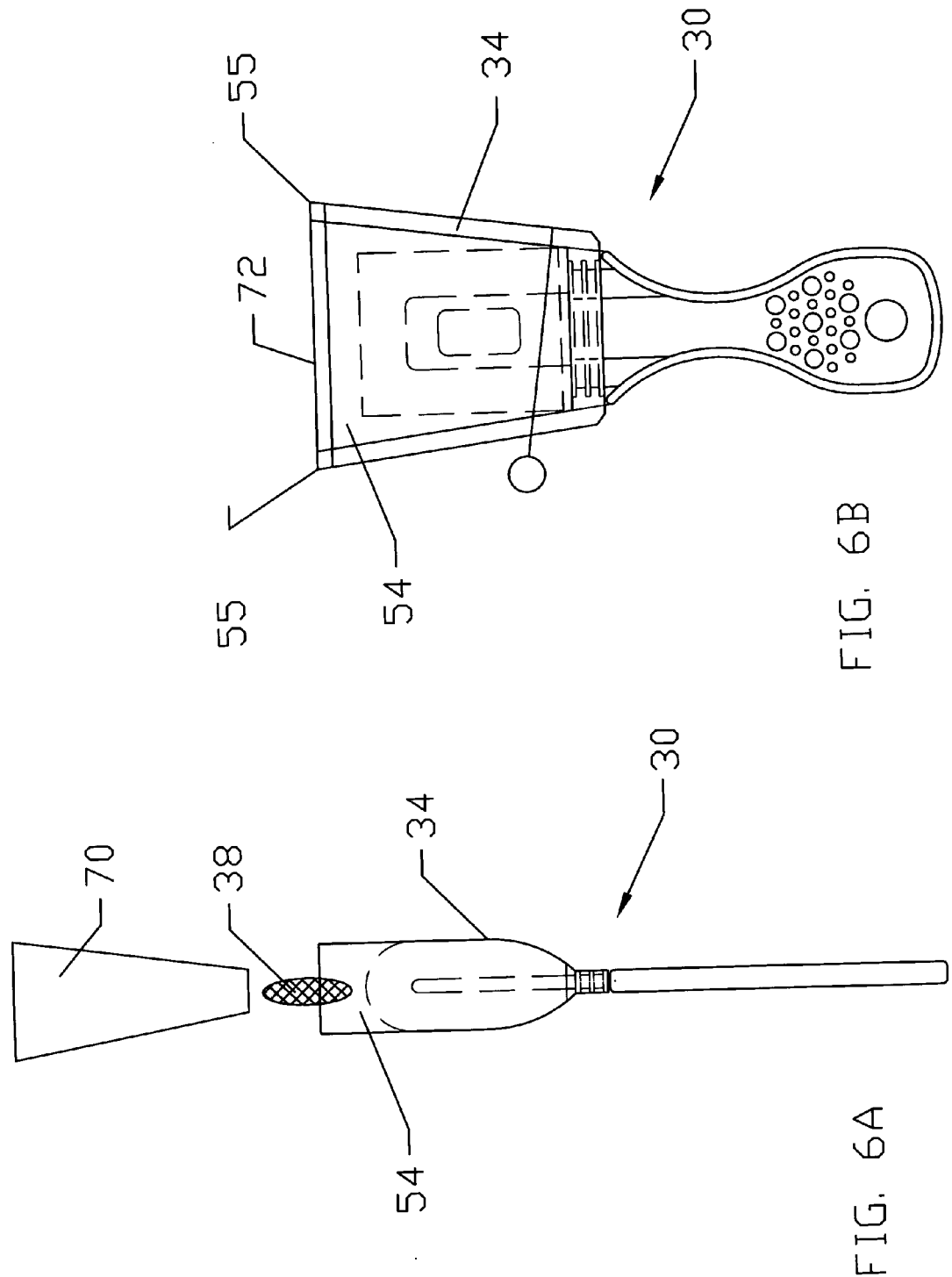

DISPOSABLE SINGLE-USE APPLICATOR

CROSS REFERENCE TO RELATED APPLICATIONS

This application claims the benefit under 35 U.S.C. 119(e) of U.S. Provisional Patent Application Ser. No. 60/406,544, filed on Aug. 28, 2002, entitled "Disposable Single-Use Applicator."

BACKGROUND OF THE INVENTION

1. Field of the Invention

The present invention relates to disposable applicators for applying fluid material on a single-use basis.

2. Description of the Prior Art

By way of background, various disposable applicators for dispensing fluid material on a single-use basis have been proposed in the prior art. According to one prior art design, a disposable single-use applicator includes a swab, a brush or other fluid holding element that is attached to a handle and adapted to be impregnated with a fluid to be dispensed. The entire applicator, including the fluid holding element and the handle, is placed in a package that is sealed after charging the fluid holding element with a dispensable fluid to prevent loss of the fluid prior to use. When it is desired to use the applicator, the package is opened and the applicator is removed therefrom. The user grasps the handle and manipulates the fluid holding element to apply the dispensable fluid to a desired location. After the fluid is exhausted, the applicator and package can be disposed of.

It is to improving disposable applicators of the foregoing type that the present invention is directed.

SUMMARY OF THE INVENTION

The foregoing problems are solved and an advance in the art is provided by an improved disposable single-use applicator assembly. The applicator assembly includes a package that is adapted to sealably contain a dispensable fluid in and around a fluid carrying applicator until the fluid is ready to be applied to a surface during use. The applicator has a handle and a fluid holding element at a first end portion of the handle. Prior to use, the fluid holding element is disposed in the package and a second end portion of the handle, adapted to be held by a user, extends clear of the package. A hermetic closure is provided between an intermediate portion of the handle and a first end portion of the package. A second end portion of the package extends past the tip end of the fluid holding element. The package has a breakable portion proximate to the hermetic closure to allow the fluid holding element to be exposed for use. The second end portion of the package initially has an opening that can be used for introducing a dispensable fluid into the package during manufacture of the applicator assembly, and then sealed to contain the fluid therein until subsequent use.

BRIEF DESCRIPTION OF THE DRAWING

The foregoing and other features and advantages of the invention will be apparent from the following more particular description of preferred embodiments of the invention, as illustrated in the accompanying Drawing in which:

FIG. 1 is a front elevational view showing a disposable applicator assembly in accordance with a first embodiment of the invention in which the applicator assembly is charged with a fluid and fully sealed for subsequent use; and FIG. 2 is a cross-sectional view taken along line 2—2 in FIG. 1;

FIG. 3 is a front elevational view showing a disposable applicator assembly in accordance with a second embodiment of the invention in which the applicator assembly is not yet charged with a fluid and has an opening in the package adapted to receive such fluid; and FIG. 4 is a cross-sectional view taken along line 30—30 in FIG. 3;

FIG. 5 is a cross-sectional view of the package end of the applicator assembly of FIG. 3 taken along line 5—5;

FIG. 6A is a diagrammatic view of a system for charging the applicator assembly of FIG. 3 with a dispensable fluid;

FIG. 6B is a front elevational view of the applicator assembly of FIG. 3 in which the package is charged with a dispensable fluid and the opening in the package is sealed.

DETAILED DESCRIPTION OF PREFERRED EMBODIMENTS

Figure 7:
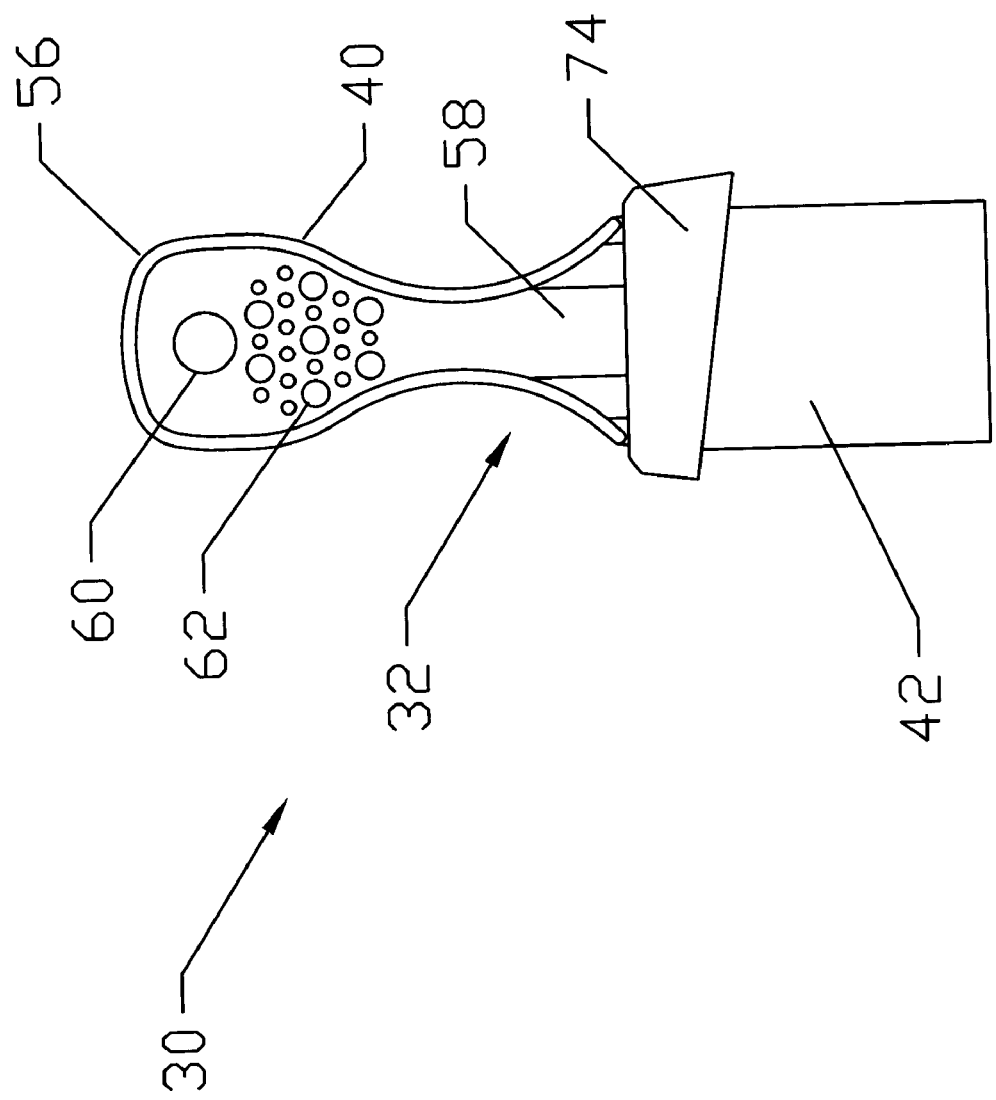
FIG. 7 is a front elevational view of the applicator assembly in FIG. 3 with the package removed.

Turning now to the figures, wherein like reference numerals represent like elements in all of the several views, FIGS. 1 and 2 illustrate a disposable applicator assembly 2 constructed in accordance with a first embodiment of the invention. The applicator assembly 2 includes a package 4 that sealably contains a dispensable fluid 6 in and around a fluid carrying applicator 8. The package 4 can be made from any suitable material that is impervious to the fluid 6, including foil, plastic or other flexible (or non-flexible) materials. The fluid 6 can be for any purpose including medical applications (e.g., wound treatment, etc.), business applications (e.g., typographic correction, etc.), or industrial applications (e.g., lubrication, etc.).

The applicator 8 has a handle 10 and a fluid holding element 12 that is laminated, adhesively bonded or otherwise affixed to the handle. The handle 10 can be formed from plastic, wood or other suitable material. The fluid holding element 12 can be implemented as a brush or can be formed as a foam member using a suitable polymeric (e.g., urethane) open cell (or closed cell) foam. Other materials capable of holding a fluid may also be used.

A first end portion 14 of the handle 10 mounts the fluid holding element 12, and is disposed in the package 4 so that the fluid holding element is in contact with and impregnated by the dispensable fluid 6. An aperture 15 can be provided in the handle's first end portion to strengthen the attachment of the fluid holding element thereto. An intermediate portion 16 of the handle 10 is appropriately configured to be attached by adhesive bonding, ultrasonic welding or the like to a first end portion 18 of the package 4. More particularly, the handle's intermediate portion 16 is defined by relatively flat upper and lower surfaces and non-tapered sides that allow a hermetic closure (seal) to be established between the handle's intermediate portion and the package's first end portion 18. To facilitate separation of the package 4 from the applicator 8, the package is provided with a breakable portion in the form of a frangible strip seal 20 located in the vicinity of the package's first end portion 18. It will be appreciated that other breakable designs (e.g. a tearable package seam provided by a line of partial perforations or the like) could also be used in lieu of the strip seal 20. A second end portion 21 of the package 4 extends from the package's breakable portion past the tip end of the fluid holding element 12.

A second end portion 22 of the handle 10 extends clear of the package 4. This portion of the handle 10 is adapted to be held by a user. Because it extends clear of the package 4, the handle's second end portion 22 is useful for point-of-purchase display or the like. To that end, the handle's second end portion 22 can be formed so as to be thin in one dimension (see FIG. 2) and relatively wide in another dimension (see FIG. 1). The relatively wide dimension of the handle's second end portion 22 provides a location 24 for applying a name, trademark or other identifier. The handle's second end portion 22 can be formed with a hole or other opening 26 so that the applicator assembly 2 can be placed on a display hook or the like. A pair of raised ridges 28 or other grip enhancing surface configuration can also be formed on the handle's second end portion 22 to facilitate gripping of the handle 10 by a user during use.

To use the applicator assembly 2, the strip seal 20 is torn off, the applicator 8 is separated from the package's second end portion 21 to expose the fluid holding element 12, and the dispensable fluid 6 that is impregnated in the fluid holding element is applied to a desired location. The package's second end portion 21 can be disposed of after opening, or it could be saved for possible replenishment of the fluid holding element 12 if any fluid remains in the package. After all of the dispensable fluid 6 is spent, the package's second end portion 21 and the applicator 8 can both be disposed of.

Turning to FIGS. 3–5, another embodiment of the invention is illustrated in which a disposable applicator assembly 30 includes an applicator 32 and an open-ended package 34 that is not yet charged with a fluid. The package 34 has an opening 36 that is provided to receive a fluid 38 (see FIG. 6A) to be introduced within the package in a future process. As in the case of the first embodiment described above, the package 34 can be made from any suitable material that is impervious to the fluid to be contained therein, including foil, plastic or other flexible (or non-flexible) materials. Moreover, the fluid can be for any purpose including painting/sealing, medical applications (e.g., wound treatment, etc.), business applications (e.g., typographic correction, etc.), or industrial applications (e.g., lubrication, etc.).

The applicator 32 has a handle 40 and a fluid holding element 42 that is laminated, adhesively bonded or otherwise affixed to the handle. The handle 40 can be formed from plastic, wood or other suitable material. As in the case of the first embodiment described above, the fluid holding element 42 can be implemented as a brush or can be formed as a foam member using a suitable polymeric (e.g., urethane) open cell (or closed cell) foam. Other materials capable of holding a fluid may also be used.

A first end portion 44 of the handle 40 mounts the fluid holding element 42, and is disposed in the package 34 so that the fluid holding element 42 can be in contact with and impregnated by a dispensable fluid when the package 34 is filled. An aperture 45 can be provided in the handle's first end portion 44 to strengthen the attachment of the fluid holding element 42 thereto. An intermediate portion 46 of the handle 40 is appropriately configured to be attached by adhesive bonding, ultrasonic welding or the like to a first end portion 48 of the package 34. More particularly, the handle's intermediate portion 46 is defined by relatively flat upper and lower surfaces and non-tapered sides that allow a hermetic closure (seal) to be established between the intermediate portion 46 and the package's first end portion 48. To facilitate separation of the package 34 from the applicator 32, the package 34 is provided with a breakable portion in the form of a frangible strip seal 50 located in the vicinity of the package's first end portion 48.

As shown in FIG. 3, the breakable portion can be angled obliquely relative to the hermetic closure. Alternatively, these elements could be parallel to each other. The strip seal 50 can be constructed with a tab 52 adapted for grasping and pulling to break strip seal. It will be appreciated that other breakable designs (e.g. a tearable package seam provided by a line of partial perforations or the like) could also be used in lieu of the strip seal 50. The package 34 has an open, unsealed second end portion 54 to allow future filling of the package with the dispensable fluid. The package's second end portion 54 extends from the breakable portion thereof past the tip end of the fluid holding element 42 to the opening 36. A pair of seams 55 extend along the length of the package 34 and exemplify the fact that the package can be formed from two sheets of material that are seamed together (e.g., via adhesive bonding, ultrasonic welding or the like) to form a fluid containing enclosure, as best shown in FIG. 5. It will be seen in FIG. 3 that the seams 55 taper outwardly from the package's first end portion 48 to the opening 36. This allows an increased quantity of fluid to be introduced into the package 34 than if the seams 55 were parallel to each other.

A second end portion 56 of the handle 40 extends clear of the package 34 so that the applicator 32 can be held during use. This design also allows the handle's second end portion 56 to be used for point-of-purchase display or the like. To that end, the handle's second end portion 56 is preferably thin in one dimension (see FIG. 4) and relatively wide in another dimension (see FIG. 3). The relatively wide dimension of the handle's second end portion 56 provides a location 58 for applying a name, trademark or other identifier. The handle's second end portion 56 may be formed with a hole or other opening 60 so that the applicator assembly 30 can be placed on a display hook or the like. A plurality of raised protrusions 62 or other grip enhancing surface configuration may also be formed on the handle's second end portion 56 to facilitate gripping of the handle 40. A flange 63 is also shown to extend around the edge of the handle's second end portion 56. Note that the flange 63 terminates at the handle's intermediate portion 46 so as not to interfere with the hermetic closure.

As shown in FIGS. 6A and 6B, to fill the applicator assembly, the dispensable fluid 38 is introduced into the package's second end portion 54 via the opening 36 a suitable conventional dispenser 70. The opening 36 is then hermetically sealed at 72 to sealably contain the fluid 38 within the package 34.

To use the filled applicator assembly 30, the tab 52 is grasped, the strip seal 50 is torn off, the applicator 32 is separated from the package's second end portion 54 to expose the fluid holding element 42, and the dispensable fluid 38 that is impregnated in the fluid holding element is applied to a desired location. As shown in FIG. 7, a residual portion 74 of the package 34 remains attached to the handle 40 of the applicator 32, and provides a drip cup that prevents dripping of the dispensable fluid 38 onto the handle's second end portion 56 when the fluid holding element 42 is elevated relative thereto. The package's second end portion 54 can be disposed of after opening, or it could be saved for possible replenishment of the fluid holding element 42 if any fluid remains in the package 34. After all of the dispensable fluid 38 is spent, the package's second end portion 54 and the applicator 32 can both be disposed of.

Accordingly, an improved disposable single-use applicator has been disclosed. While various embodiments of the invention have been shown and described, it should be apparent that many variations and alternative embodiments could be implemented in accordance with the invention. It is understood, therefore, that the invention is not to be in any way limited except in accordance with the spirit of the appended claims and their equivalents.

What is claimed is:

1. A disposable single-use applicator assembly, comprising:
- a package containing a fluid to be dispensed;
- said package comprising a flexible or non-flexible material that defines a fluid holding interior region of said package;
- an applicator for dispensing said fluid, said applicator having a handle and a fluid holding element at a first end portion of said handle;
- said fluid holding element being disposed in said package interior region;
- a hermetic closure attaching a first end portion of said package to an intermediate portion of said handle, said hermetic closure hermetically sealing said package to said handle such that said fluid holding interior region is hermetically sealed;
- a second end portion of said handle extending clear of said package;
- said package having a breakable portion proximate to said hermetic closure to allow said fluid holding element to be uncovered for use; and
- said breakable portion comprising a frangible seal formed in said package material that allows said package material to be broken.

2. A disposable single-use applicator assembly in accordance with claim 1 wherein said handle second end portion is relatively thin in one dimension and relatively wide in another dimension and includes a location for applying a name, trademark or other identifier.

3. A disposable single-use applicator assembly in accordance with claim 1 wherein said handle second end portion includes a hole or other opening to facilitate placement of said applicator assembly on a display hook.

4. A disposable single-use applicator assembly in accordance with claim 1 wherein said handle second end portion includes a grip enhancing surface.

5. A disposable single-use applicator assembly in accordance with claim 1 wherein said handle intermediate portion is defined by relatively flat first and second surfaces and non-tapered sides that facilitate formation of said hermetic closure.

6. A disposable single-use applicator assembly in accordance with claim 1 wherein said hermetic closure comprises one of an adhesive bond or ultrasonic weld bond.

7. A disposable single-use applicator assembly in accordance with claim 1 wherein said fluid holding element comprises a urethane foam material.

8. A disposable single-use applicator assembly in accordance with claim 1 wherein said breakable portion comprises a strip seal.

* * * * *